United States Patent [19]

Blaze

[11] Patent Number: 4,692,685
[45] Date of Patent: Sep. 8, 1987

[54] ELECTRICAL MEASURING APPARATUS, AND METHODS FOR DETERMINING THE CONDITION OR IDENTITY OF BIOLOGICAL MATERIAL

[76] Inventor: Kevin L. Blaze, 29 Severn Street, Box Hill North, Victoria, Australia

[21] Appl. No.: 711,795

[22] Filed: Mar. 14, 1985

[30] Foreign Application Priority Data

Mar. 14, 1984 [AU] Australia ............................. PG4064

[51] Int. Cl.[4] ........................................... G01R 27/26
[52] U.S. Cl. .............................. 324/61 QS; 324/65 R; 324/61 R
[58] Field of Search .............. 324/61 R, 65 R, 61 QS; 435/291

[56] References Cited

U.S. PATENT DOCUMENTS

| | | | |
|---|---|---|---|
| 2,759,149 | 8/1956 | Hart | 324/65 R |
| 3,155,902 | 11/1964 | Walls | 324/61 R |
| 3,255,410 | 6/1966 | Norwich | 324/61 R |
| 3,320,946 | 5/1967 | Dethloff et al. | 324/61 R |
| 3,323,047 | 5/1967 | Martin et al. | 324/61 R |
| 3,688,309 | 8/1972 | Volberg | 340/421 |
| 3,746,975 | 7/1973 | Maltby | 324/61 R |
| 3,766,471 | 10/1973 | Pullman | 324/65 R |
| 4,019,132 | 4/1977 | Loch | 324/65 R |
| 4,259,633 | 3/1981 | Rosenau | 324/65 R |
| 4,408,128 | 10/1983 | Fujita | 324/65 R |

OTHER PUBLICATIONS

*The Electrical Assessment of Plant Health and Injury*, by Greg Moore and Kevin Blaze, 3/1980.
*The Effects of High Temperatures on the Growth and Physiology of E. Obliqua L'Herit Seedlings*, Thesis by Gregg Moore, University of Melbourne, Nov. 1981.

Primary Examiner—Samuel Scott
Assistant Examiner—Noah Kamen
Attorney, Agent, or Firm—Sughrue, Mion, Zinn, Macpeak, and Seas

[57] ABSTRACT

This invention relates to a measurement system which applies voltage signals of different frequencies across a biological sample. The frequencies are chosen such that both resistance and capacitance are significant components of the measured impedance. The state of the biological sample is reflected in the admittance ratio for two frequencies.

10 Claims, 3 Drawing Figures

ELECTRICAL MEASURING APPARATUS, AND METHODS FOR DETERMINING THE CONDITION OR IDENTITY OF BIOLOGICAL MATERIAL

BACKGROUND OF THE INVENTION

This invention relates to apparatus which has particular but by no means exclusive application to the determination of the condition or identity of material of biological origin.

It is known to assess the condition of material of biological origin by passing an electrical current through a portion of the material and measuring a selected electrical parameter. Direct, alternating and pulsed current have variusly been proposed and a well known commerical instrument measures the voltage developed across a bi-contact probe (U.S. Pat. No. 3,864,627) by a constant pulsed current.

In a further development of these principles, it is known that for a particular specimen of vegetation, the ratio of the electrical impedance of a fixed length of the vegetation to an applied current of low frequency, e.g. 1 kHz, to the impedance of the same length of the vegetation to a current of high frequency, e.g. 10 kHz, hereinafter referred to as the "impedance ratio", is reduced as the condition of the specimen deteriorates due to stress such as heat or decapitation. With some species of plant, for example, the impedance ratio of a healthy plant is approximately 3:1, whereas the impedance ratio of a dead plant is approximately 1:1.

An instrument for measuringthe impedance at two frequencies and thereby determining the impedance ratio is described in de Plater and Greenham P1 Physiol 34:661-667 (1959). This instrument comprises a wide range AC bridge and its use to determine the impedance ratio has the advantages that such ratio is largely unaffected by moisture content and that when using a probe in homogenous tissue the impedance ratio is independent of the depth of probe insertion; depth of insertion must be kept constant for single reading instruments. However, the bridge instrument requires balancing twice during each determination, a requirement which is inconvenient under field conditions because in the implement of de Plater and Greenham up to 11 controls may require adjustment and the balancing operation may not be entirely objective.

To meet these problems, it has been proposed (Ph.D. thesis by Moore, University of Melbourne 1981) to employ an arrangement in which an AC voltage is applied to the probe and the voltage drop across as reference resistor is measured, that resistor being part of a two-resistor divider of which the plant is the other resistor. However, as a result of using a divider resistor, this arrangement has a hyperbolic response to impedance so that the meter measures impedance in arbitrary and non-linear units.

U.S. Pat. No. 4,408,128 to Fujita describes a moisture meter in which the electrical resistance of a grain or wood sample is measured by applying a DC or very low frequency AC signal (80 Hz) across a probe contactable with the sample, logarithmically scaling the resultant current by means of an operational amplifier having its inputs in series with the probe to produce a display value linearly related to moisture content. It is to be noted that Fujita, in determining moisture content, is concerned strictly with resistance of the sample and hence proposes a DC or 80 Hz AC applied voltage. Biological tissue may be represented by a resistor in parallel with a capacitor. Measurements made by the present applicant indicate ranges of 1 k$\Omega$ to 200 k$\Omega$ for the resistance component and 0.05 nF to 10 nF for the capacitance component. At these values and a frequency of 80 Hz, there would be no effective capacitive contribution to impedance. Fujita moreover relies upon a logarithmic relationship between resistance and moisture content.

In contrast to these features of Fujita, applicant's concern for assessing plant condition or identity requires an examination of both the resistance and capacitance contributions to the impedance and need take no account of any logarithmic relationship with respect to resistance. Furthermore, it is known that the result must be accurate to somewhat better than $\pm 5\%$ for statistically significant conclusions to be drawn in regard to tissue condition or identity: such accuracy is not feasible with the circuit configuration of Fujita. To identify differences between biological samples, a statistically significant difference must be shown. This is usually chosen to be at the 95% level although higher levels may sometimes be used. Errors must therefore be substantially less than 5%. Finally, the use of DC voltage as proposed by Fujita is believed unacceptable in biological tissue as it causes irreversible destruction of tissue, even at lower levels.

SUMMARY OF THE INVENTION

It is therefore an object of the invention to provide improved apparatus which may be utilized in assessing the condition or identity of material of biological origin but which is an advance over the Moore arrangement, preferably by providing measurements in standard electrical units.

The invention accordingly provides apparatus for determining an impedance ratio for biological tissue for assessing the condition or identity of the tissue, comprising:

a pair of electrical conductors connectible to the respective spaced contacts of a probe, between which contacts tissue is disposed in use of the apparatus;

means to generate a constant AC voltage at each of two distinct frequencies at which both the resistance and the capacitance of the tissue between said contacts are significant components of the impedance therebetween;

voltage stabilization means coupled to said generation means to maintain the amplitude of said AC voltage at the two frequencies at the same accurately constant value;

buffer means in series with and between said generation means and one of said conductors to minimize the loading affect of the impedance of the tissue on the impedance of the generating means;

amplifier means coupled to the other said conductor to generate a voltage signal directly proportional to the current through said tissue between the probe contacts on application of said AC voltage across a portion of the circuit which includes the tissue and the amplifier means; and means to convert said voltage signal to a DC output, which is a measure of the admittance of the tissue between the probe contacts, the impedance ratio for the two frequencies being thereby determinable from the respective DC outputs at the two frequencies.

The invention also affords a method of determining an impedance ratio for sample biological tissue, for assessing the condition or identity of the tissue, comprising:

applying an AC voltage of accurately constant amplitude across the sample at one frequency then another, at which frequencies both the resistance and the capacitance of the sample are significant components of the impedance therebetween;

measuring the respective currents across the sample and outputting voltage signals indicative of the value of the respective currents;

converting each said voltage signal to a DC output, which is a measure of the admittance across the sample; and determining the impedance ratio for the two frequencies from said DC outputs.

BRIEF DESCRIPTION OF THE DRAWINGS

The invention will be further described, by way of example only, with reference to the accompanying drawings, in which.

DETAILED DESCRIPTION OF THE INVENTION

Figure 1:
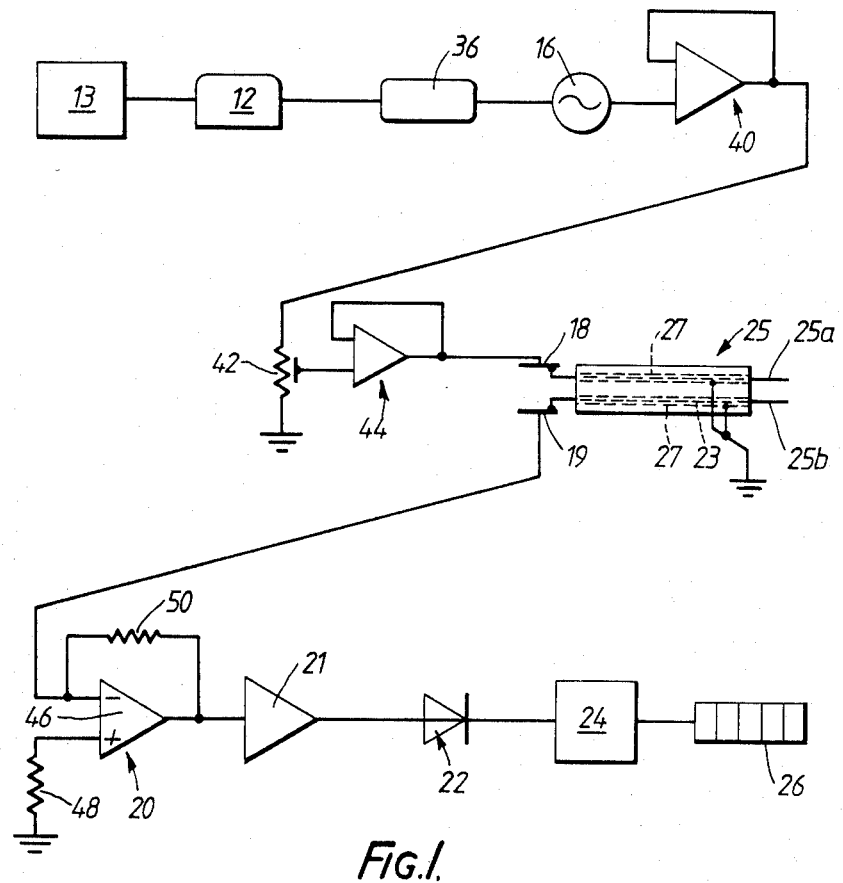
FIG. 1 is a block schematic of apparatus according to the invention, shown with a probe in position.

The illustrated arrangement includes a battery power pack 12 and associated charging circuitry 13, a waveform generator or oscillator 16 set to generate a sinusoidal AC voltage at two selectable frequencies, probe contacts 18, 19, a linear current-to-voltage converter 20 having a virtual ground configuration, AC to DC converter 22, an optional ratiometric segment 24 and a digital display 26. In use of the apparatus, a probe 25 with spaced parallel needle electrodes 25a, 25b projecting from an insulating body 23 is coupled to contacts 18, 19, and the electrodes caused to penetrate a sample of biological tissue, e.g. the trunk or a branch of plant. The electrodes 25a, 25b are separately shielded by respective conductive screens 27 which are embedded in support body 23 and are commonly earthed. An AC voltage is applied, first at 1 kHz, then at 10 kHz, across the probe contacts. Respective voltage signals directly proportional to the current through the sample are output by converter 20, converted in turn to DC at 22, their quotient or ratio determined by segment 24 and an indication of the result displayed at 26. If segment 24 is not provided, the output of converter 22 is displayed at 26. It will be understood that the output of converter 22 is strictly a measure of admittance, the inverse of impedance, in view of the linear determination of curent by converter 20.

Figure 2:
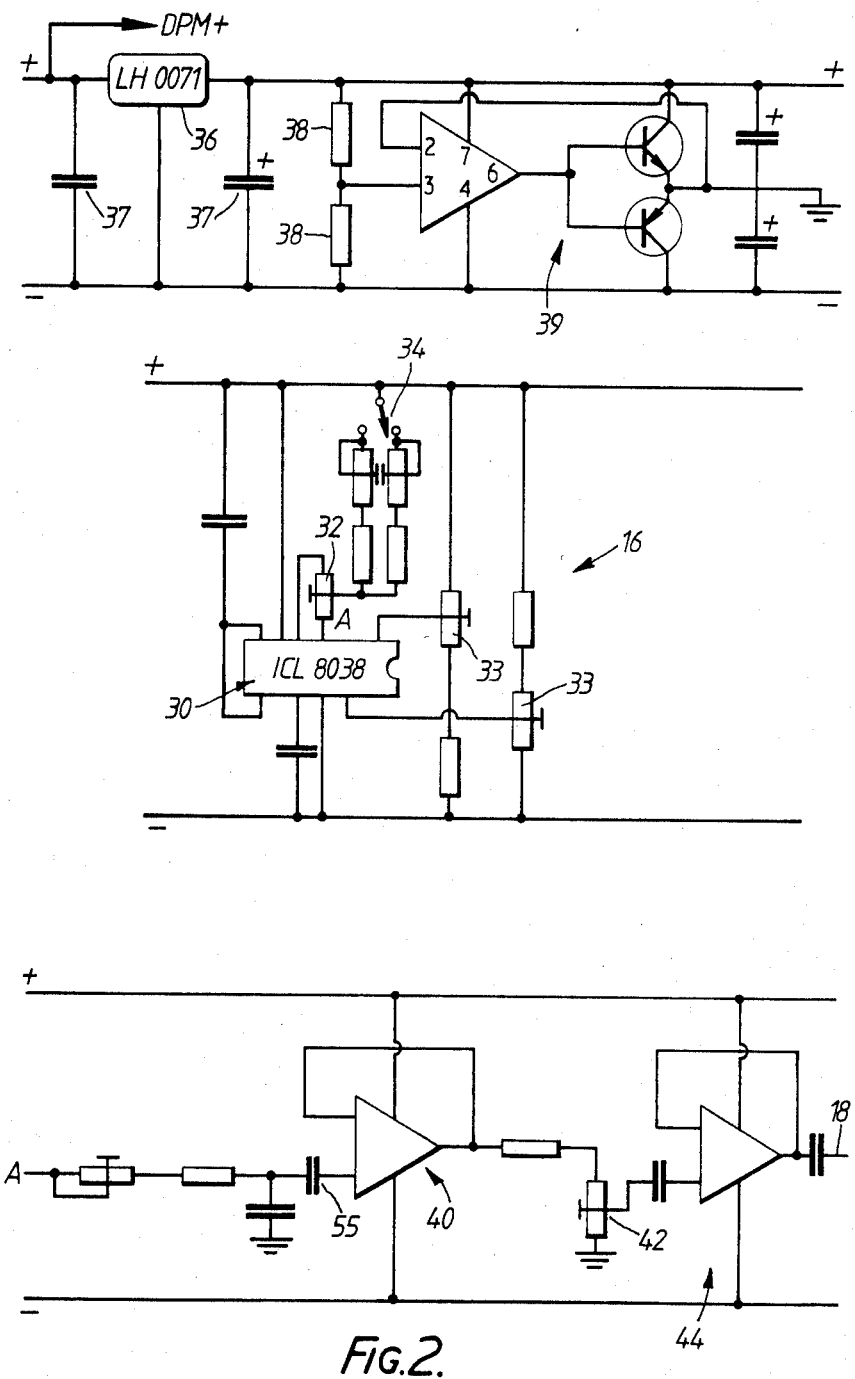
FIGS. 2 and 3 are respectively more detailed circuit diagrams for the voltage supply and measurement segments of the circuit depicted in FIG. 1, the ratiometric segment being omitted from FIG. 3.

Waveform generator 16 is depicted in greater detail in FIG. 2. The principal component is an oscillator chip 30, e.g. ICL 8038. A trio of trimming potentiometers 32, 33, provide present adjustments for respectively optimizing waveform symmetry and minimizing distortion. A manual switch 34 permits selection of the two operating frequencies, in this case 1 kHz and 10 kHz; this switchmight be replaced by e.g. a CMOS switch in a mroe sophisticated arrangement used in the case of direct ratio readout.

It is important that generator 16 be arranged to generate AC signals of at least two discrete frequencies for which the resistance and capacitance between contacts 18, 19 across the sample at the probe are both significant components of the impedance between the contacts. It is generally understood that both components are affected by elements of tissue condition, that resistance indicates moisture content and ionic strength, while capacitance indicates membrane and cell integrity. The frequencies are preferably in the range 500 Hz to 100 kHz, and the two selected frequencies are preferably at least an order of magnitude different.

In order to ensure the aforementioned somewhat better than 5% required precision in the final ratio, a precision voltage regulator 36, e.g. LH 0071 of National Semiconductors is coupled between battery pack 12 and generator 16. Stability is enhanced by capacitors 37 across the DC bus to either side of regulator 36. The supplied DC voltage is accurately equally divided by equal resistors 38 and buffered and filtered at 39 for presentation to generator 16.

The AC output fromt he waveform generator 16 is further passed to an active filter 40 for smoothing out amplitude errors arising in the generator. An adjustable resistor divider 42 is then employed to lower the applied voltage to a maximum 10 mv rms in order to minimize errors caused by power dissipation in the sample tissue which has been found to cause reading errors and irreversible damage to the tissue. This signal is then buffered by an impedance transformer 44 to minimize the loading effect of the impedance of the sample on the impedance of the generator so that loading of the output of the sample is no greater than 1%. The output of buffer 44 is to probe contact 18.

Figure 3:
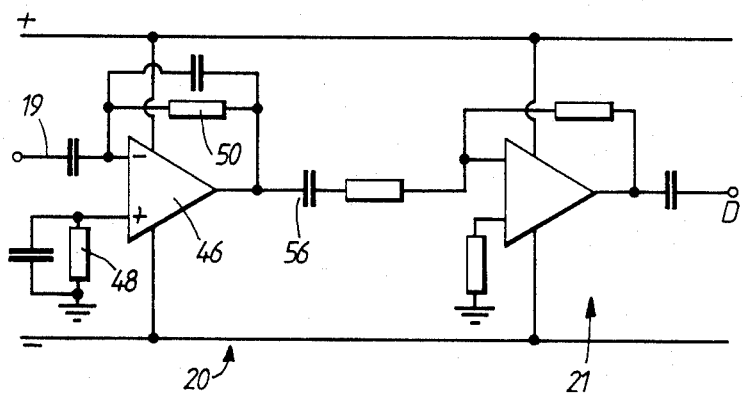
Figure 3:
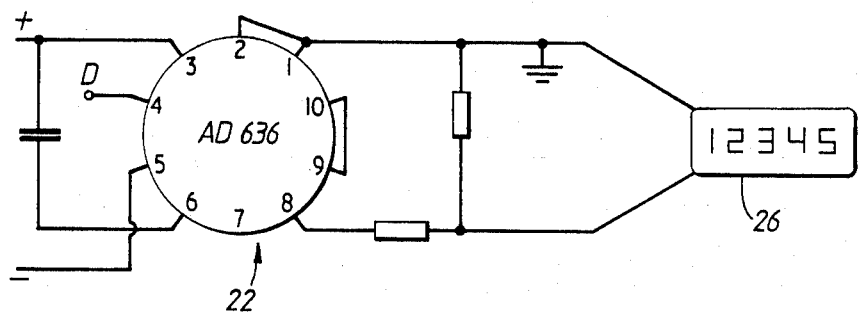

Linear current-to-voltage converter 20 comprises (FIG. 3) an operational amplifier 46, with its inverting (−) input coupled to contact 19 and its + input to ground via a balancing resistor 48. A feedback resistor 50 is also coupled to the inverting input and both resistors 48, 50 include parallel capacitors. Resistors 48, 50 are suitably both 100 ohm. The voltage output of op amp 46, which as mentioned is directly proportional to the current through the sample tissue, is fed to AC-DC converter 22 via an amplifier 21. Converter 22 may, e.g., comprise AD 636. If provided, ratiometric circuit segment 24 may use either a microprocessor or analog techniques.

Filter capacitors, e.g. those indicated at 55, 56, are placed at intervals in the circuit to filter out unwanted DC levels in the supplied, measured and derived AC signals.

By directly determining the current through the sample tissue by way of converter 20, a wide range of admittances can be measured and corresponding impedance ratios derived for a wide variety of tissues, e.g. plants, timber and meat. The apparatus thus has utility in determining the condition of plants, or in meat or timber inspection services. The range of measurable admittances is 1 μS to 2000 μS, the accuracy of both admittance readings and the subsequent ratio is better than ±1%. Power dissipation in representative plant tissue is less than 0.2 μW. Corresponding values for the arrangement of the Moore thesis are a range of 1 to 2000 arbitrary units, a ratio accuracy better than ±10% and power dissipation of less than 4 mW. It will be appreciated that, in contrast to the Moore arrangement, the apparatus of the invention measures an electrical parameter (admittance) linearly in actual electrical units (Siemens).

With respect to the aforementioned range of applicant's apparatus, by chaning only the resistor values in the converter 20 and, if necessary, the output at 18, other ranges may be read. A range switch might easily be included, but such is unnecessary for application of the apparatus to plants. A different range might be desirable, e.g., for application to meat.

I claim:

1. Apparatus for determining a measure of the admittance of biological tissue and an admittance ratio for the tissue, for assessing the condition or identity of the tissue, comprising:
   A pair of electrical conductors connectable to the respective contacts of a probe having a fixed spacing, between which contacts tissue is disposed in use of the apparatus;
   means to generate a constant AC voltage at each of two distinct frequencies at which both the resistance and the capacitance of the tissue between said contacts are significant components of the impedance therebetween;
   means to apply said constant AC voltage across said contacts first at one of said frequencies, then at the other;
   precision voltage stabilization means coupled to said generation means to maintain the amplitude of said AC voltage at the two frequencies at the same accurately constant value;
   buffer means in series with and between said voltage generation means and one of said conductors to minimize the loading effect of the impedance of the tissue on the impedance of the generating means;
   amplifier means coupled to the other said conductor, in series with tissue when disposed between said contacts, to receive the current through the tissue and to generate an output AC voltage signal directly proportional to the current through the tissue and therefore to the admittance of the tissue on application of said AC voltage across a portion of the circuit which includes the tissue and the amplifier means; and
   means to convert said output AC voltage signal to a DC output which is a measure of the admittance of the tissue between the probe contacts, the admittance ratio, for the two frequencies being thereby determinable from the respective DC outputs at the two frequencies.

2. Apparatus according to claim 1 wherein said amplifier means comprises an operational amplifier with its inputs coupled in series with said other conductor.

3. Apparatus according to claim 1 further including a display coupled to said conversion means to receive the DC output and to display an indication of its value.

4. Apparatus according to claim 1 further including a probe coupled to said electrical conductors, said probe comprising an insulating support body and a pair of parallel needle contacts having a fixed spacing therebetween projecting from said body, the respective electrodes being separately shielded and electrically connected to the respective said conductors and being capable of penetrating biological tissue.

5. Apparatus according to claim 1 wherein said means to maintain said AC voltage constant includes a precision voltage regulator in an emf supply line for said generation means.

6. Apparatus according to claim 1 wherein said AC voltage is no greater than 10 mV rms, in order to minimize errors and irreversible damage to biological tissue caused by power dissipation in the tissue.

7. Apparatus according to claim 1 further including means coupled to said conversion means to receive said DC outputs at the respective frequencies, to derive therefrom said impedance ratio and to output an indication of the value of the ratio and therefore of the condition of biological tissue between said contacts.

8. A method of determining a measure of the admittance of biological tissue and admittance ratio for the tissue, for assessing the condition or identity of the tissue, comprising:
   applying an AC voltage maintained at accurately constant amplitude by precision voltage stabilization means across the sample at one frequency than the other, at which frequencies both the resistance and the capacitance of the sample are significant components of the impedance therebetween;
   directly measuring the respective currents across the sample by amplifier converter means having a virtual ground configuration in series with the tissue to receive the current through the tissue, and outputting AC voltage signals directly proportional to the respective currents and therefore to the admittance of the tissue;
   converting each said AC voltage signal to a DC output, which is a measure of the admittance across the sample, and determining the admittance ratio for the two frequencies from said DC outputs.

9. A method according to claim 8 further comprising determining the admittance ratio for the two frequencies from said DC outputs.

10. a method according to claim 8 wherein said AC voltage is no greater than 10 mV rms, in order to minimize errors and irreversible damage to biological tissue caused by power dissipation in the tissue.

* * * * *